United States Patent
Miyake et al.

(10) Patent No.: US 7,806,822 B2
(45) Date of Patent: Oct. 5, 2010

(54) MEDICAL SYSTEM CONTROL DEVICE

(75) Inventors: Kensuke Miyake, Tokyo (JP); Chieko Aizawa, Tokyo (JP); Tsukasa Ishii, Tokyo (JP); Hiroyuki Ushifusa, Tokyo (JP); Akihiro Miyashita, Tokyo (JP)

(73) Assignee: Olympus Corporation, Tokyo (JP)

( * ) Notice: Subject to any disclaimer, the term of this patent is extended or adjusted under 35 U.S.C. 154(b) by 1023 days.

(21) Appl. No.: 11/582,571

(22) Filed: Oct. 17, 2006

(65) Prior Publication Data

US 2007/0120550 A1 May 31, 2007

Related U.S. Application Data

(63) Continuation of application No. PCT/JP2005/002142, filed on Feb. 14, 2005.

(30) Foreign Application Priority Data

Apr. 23, 2004 (JP) ............................. 2004-128488

(51) Int. Cl.
*A61B 1/00* (2006.01)
(52) U.S. Cl. ...................................... 600/101; 600/118
(58) Field of Classification Search ................. 600/101, 600/103, 118; 323/911, 371; 714/36, 12; 713/1
See application file for complete search history.

(56) References Cited

U.S. PATENT DOCUMENTS 5,678,568 A * 10/1997 Uchikubo et al. ............ 128/897
2002/0105409 A1 * 8/2002 Nakamitsu et al. ........... 340/3.1
2003/0154337 A1 * 8/2003 Ohno et al. .................. 710/260
2004/0030367 A1 * 2/2004 Yamaki et al. ................ 607/60
2004/0172011 A1 * 9/2004 Wang et al. ..................... 606/1
2005/0015215 A1 * 1/2005 Zhang .......................... 702/119
2005/0273633 A1 * 12/2005 Wilcox et al. ................ 713/300

FOREIGN PATENT DOCUMENTS

| JP | 03-284230 | 12/1991 |
| JP | 06-052128 | 2/1994 |
| JP | 09-192095 | 7/1997 |
| JP | 2001-067212 | 3/2001 |
| JP | 2003-260054 | 9/2003 |

* cited by examiner

*Primary Examiner*—John P Leubecker
(74) *Attorney, Agent, or Firm*—Scully, Scott, Murphy & Presser, P.C.

(57) ABSTRACT

A medical system control device comprises a first control unit for controlling at least a power supply to a plurality of devices configuring a medical system, a second control unit, the startup process time of which is longer than the first control unit, for controlling the entire medical system, and a storage unit for storing information at the time of an operation termination process for the medical system, which is performed by the second control unit. The first control unit controls a power supply to a predetermined device among the plurality of devices before the startup process of the second control unit is complete, according to the information stored in the storage unit in response to the power-on of the medical system.

11 Claims, 14 Drawing Sheets

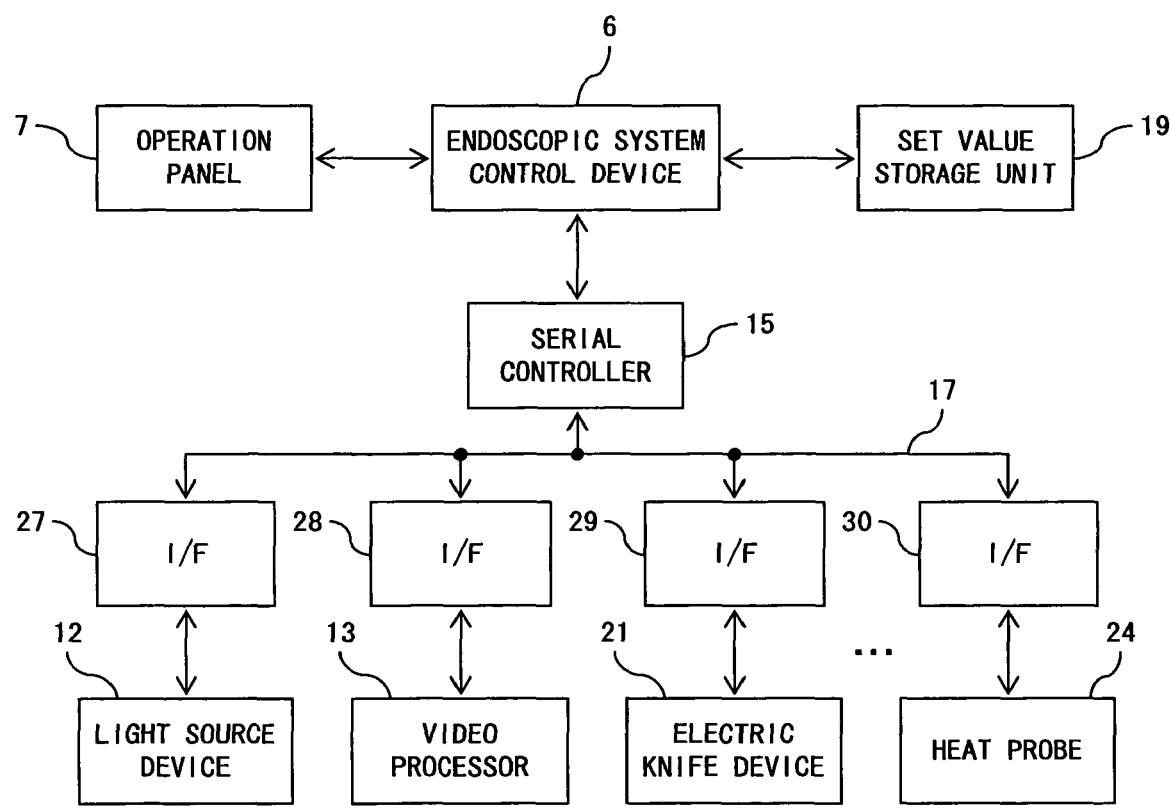
F I G. 3

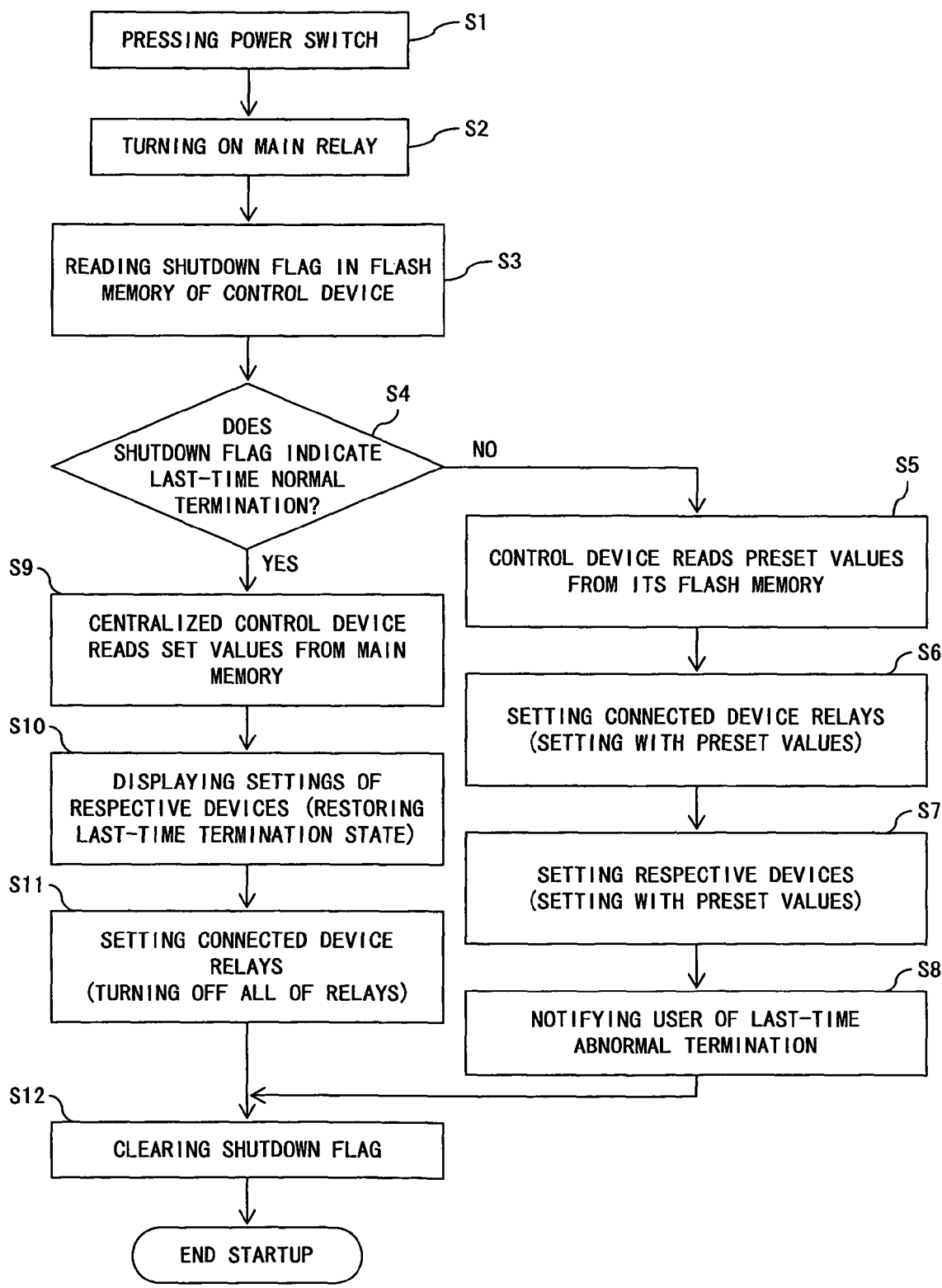
F I G. 5

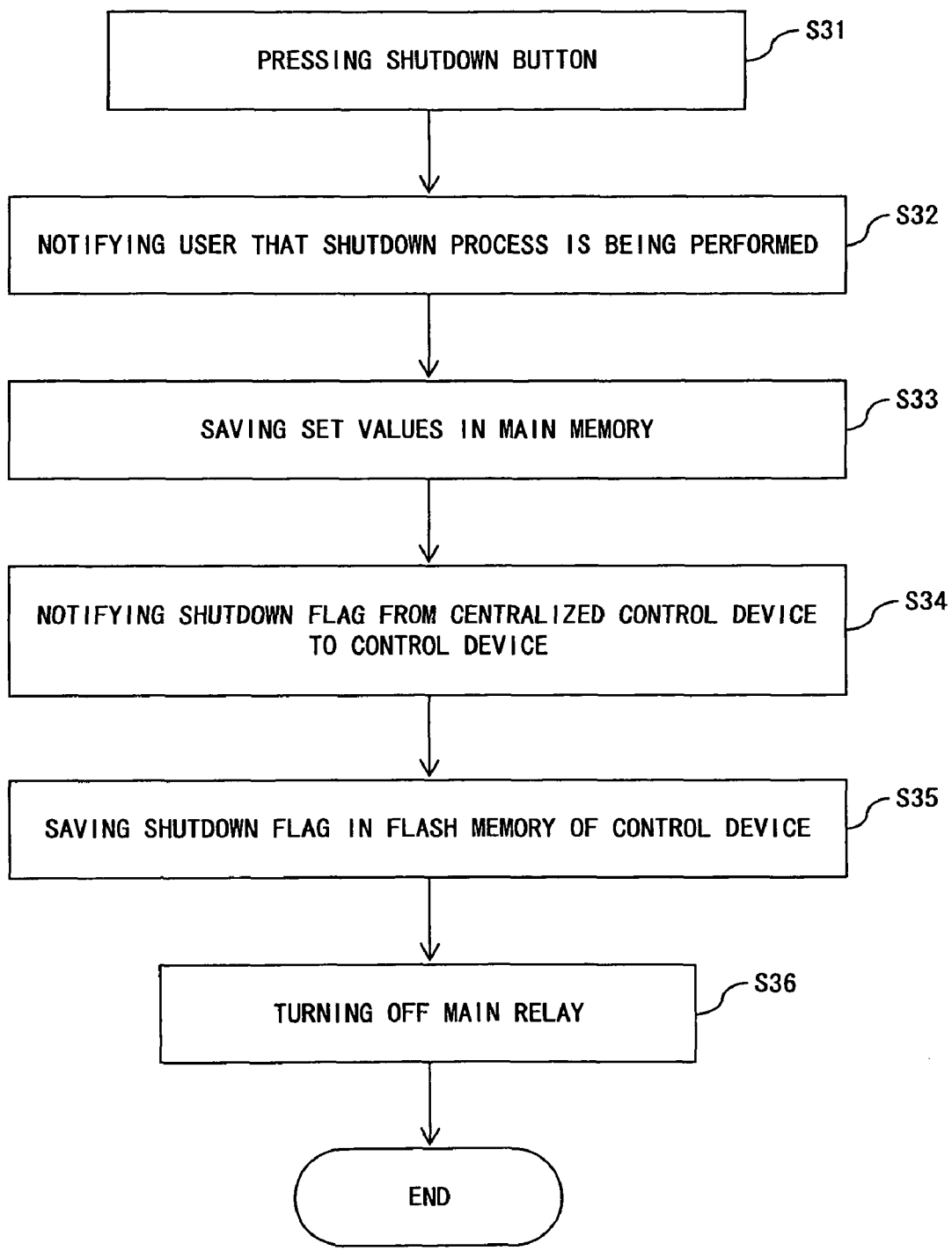
F I G. 6

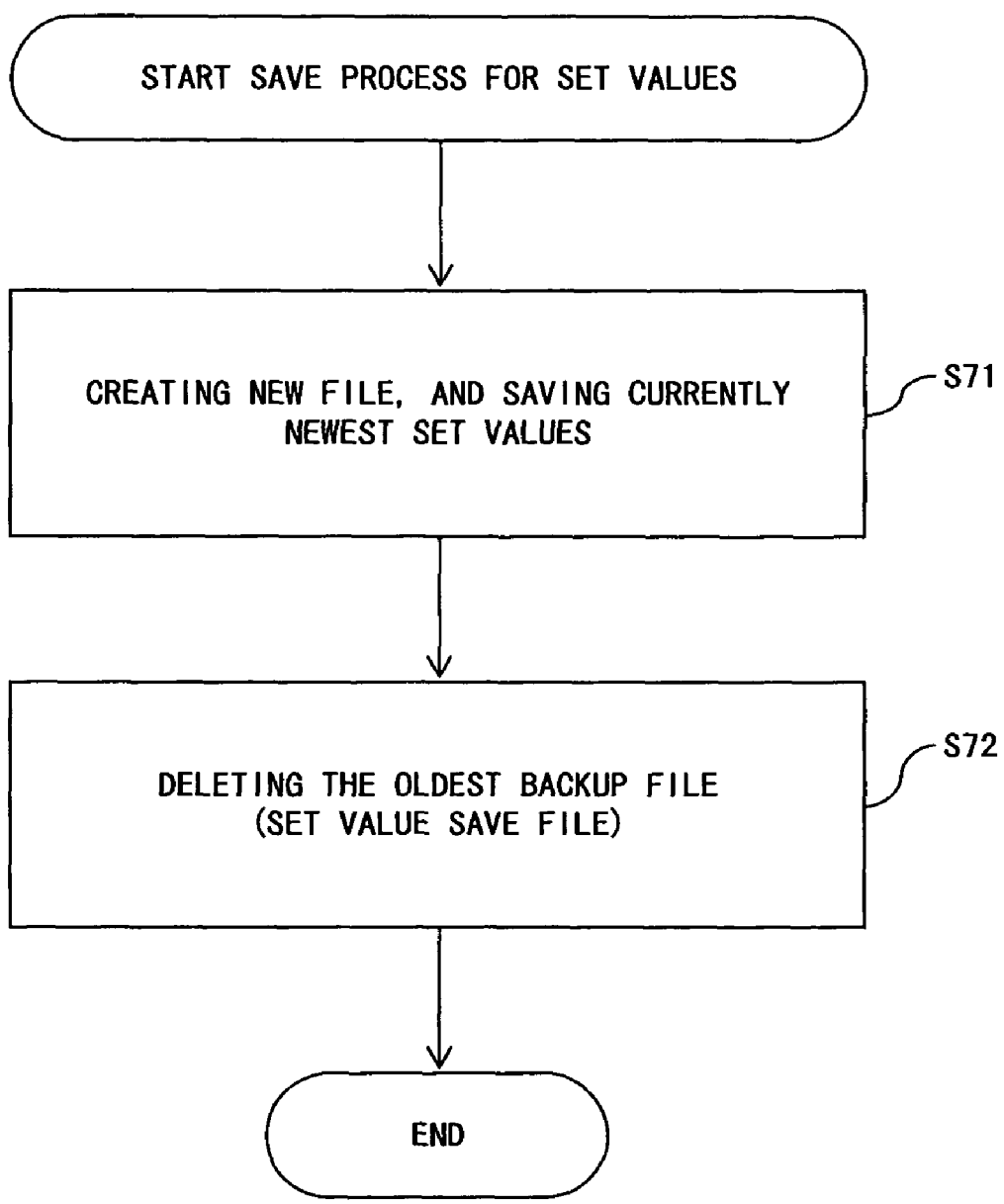
F I G. 13

MEDICAL SYSTEM CONTROL DEVICE

CROSS REFERENCE TO RELATED APPLICATIONS

This is a Continuation Application of PCT Application No. PCT/JP 2005/002142, filed Feb. 14, 2005, which was not published under PCT Article 21(2) in English.

This application is based upon and claims the benefit of priority from the prior Japanese Patent Application No. 2004-128488, filed Apr. 23, 2004, the entire contents of which are incorporated herein by reference.

BACKGROUND OF THE INVENTION

1. Field of the Invention

The present invention relates to a medical system control device for controlling the power state of a medical device such as a light source device, etc.

2. Description of the Related Art

When an endoscopic examination or therapy/treatment is made by using an endoscope, an endoscopic system is configured by collecting medical devices such as a light source device, etc. on a rack, etc., or racks on which these devices are mounted are combined to make the endoscopic examination or therapy/treatment in normal cases.

The present applicant discloses, for example, in Patent Document 1, the endoscopic system in which a plurality of devices are accommodated in one housing, and which comprises a centralized control unit for performing a centralized control for the plurality of devices, and a centralized operation unit for performing a centralized operation for the plurality of devices.

Such an endoscopic system includes diverse devices such as a light source device for supplying illumination light to a body to be examined via an endoscope, a video signal processing device (a video processor or a video system center) for processing an image signal from the endoscope, a shooting device for shooting an optical image from the endoscope, a cauterizing device (heat probe) for making a treatment by cauterizing a portion to be examined, an electric knife device for resecting a portion to be examined, an observation monitor for displaying an endoscopic. image, a bed on which a patient is placed at the time of an examination, and the like. This system is configured by combining these peripheral devices depending on a purpose.

As a centralized operation unit for performing a centralized operation for the peripheral devices, an operation screen display unit such as a liquid crystal display for displaying operation switches, and an input detection unit such as a touch panel, etc. arranged on the operation screen display unit are provided. On the operation screen display unit, an operation screen is displayed. With the press (or touch) of a target operation switch on the operation screen, the position pressed on the touch panel is detected to input an operation instruction to the centralized control unit, whereby a corresponding device is controlled by the centralized control unit.

With such a configuration, centralized operation and control can be performed for the peripheral devices when an endoscopic examination or therapy/treatment is made. Additionally, the running states of the devices can be verified, whereby a load on an operator, which is imposed when each device is operated, can be reduced, and operability can be improved. Furthermore, an endoscopic system can be configured by combining devices depending on a purpose even if the devices to be used are different, whereby centralized control can be performed for the peripheral devices according to the configuration of the system.

Patent Document 1: Japanese Published Unexamined Patent Application No. H3-284230

SUMMARY OF THE INVENTION

A medical system control device according to the present invention comprises a first control unit for controlling at least a power supply to a plurality of devices configuring a medical system, a second control unit, the startup process time of which is longer than the first control unit, for controlling the entire medical system, and a storage unit for storing information at the time of an operation termination process for the medical system, which is performed by the second control unit, wherein the first control unit controls a power supply to a predetermined device among the plurality of devices before the startup process of the second control unit is complete, according to the information stored in the storage unit in response to the power-on of the medical system.

A medical system startup control method according to the present invention, which is used when a medical system is powered on, comprises: a storing step of storing information about whether or not an operation termination process in the medical system is normally performed, a determining step of determining whether or not the operation termination process is normally performed by reading the information when the medial system is powered on, a first startup process step of controlling a power supply to a predetermined device if the operation termination process is determined not to be normally performed in the determining step, and a second startup process step of performing a startup process, which takes longer time than the first startup process step, in accordance with a case of a normal termination if the operation termination process is determined to be normally performed in the determining step.

BRIEF DESCRIPTION OF THE DRAWINGS

FIG. 3 is a block diagram showing a functional configuration when peripheral devices are controlled with an operation panel in the first preferred embodiment;

FIG. 5 is a flowchart showing a startup process performed by the endoscopic system control device in the first preferred embodiment;

FIG. 6 is a flowchart showing a shutdown process performed by the endoscopic system control device in the first preferred embodiment;

FIG. 13 is a flowchart showing a save process for a set value file in the third preferred embodiment.

DESCRIPTION OF THE PREFERRED EMBODIMENTS

Figure 1:
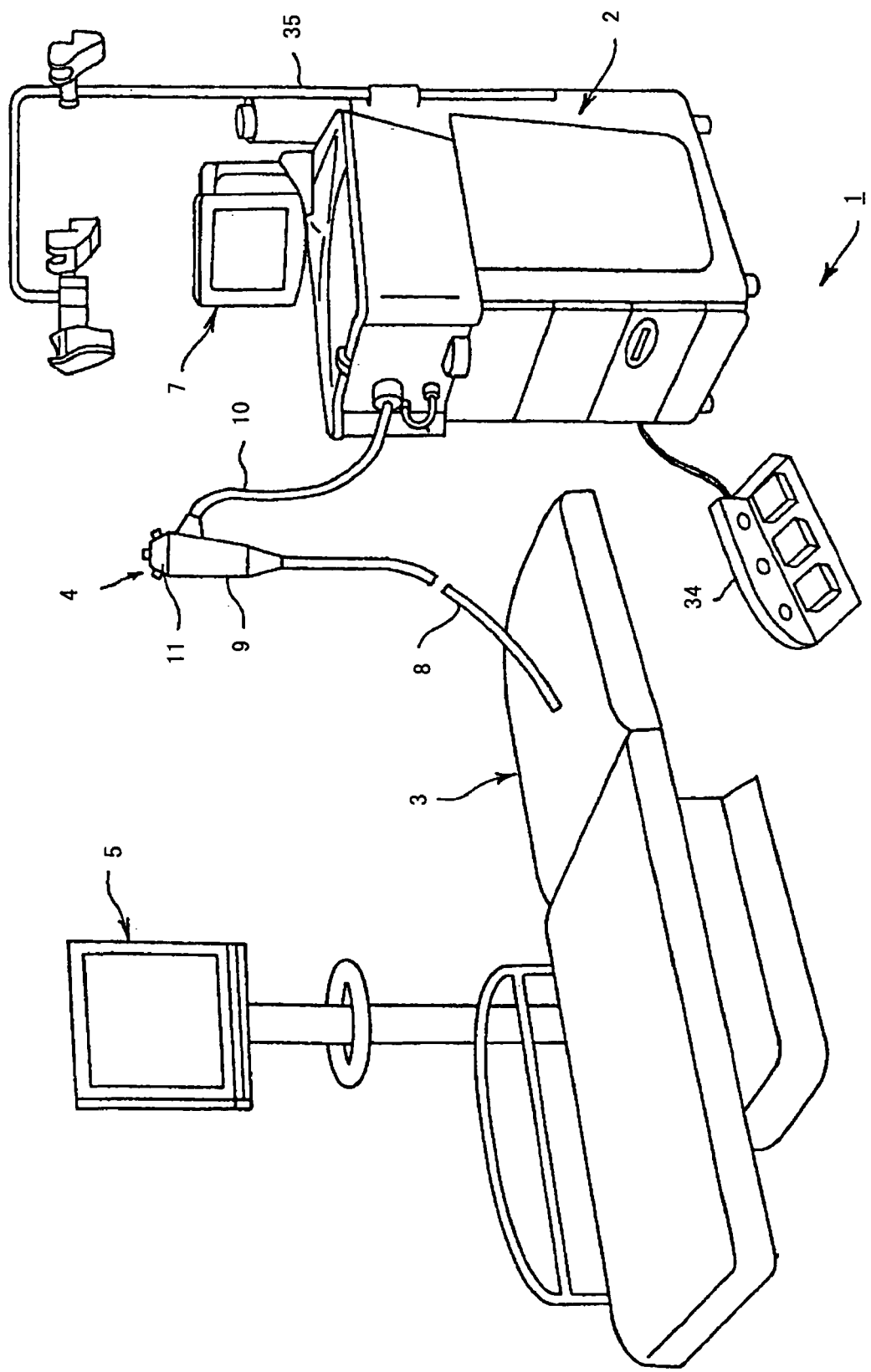
FIG. 1 shows the outside configuration of an endoscopic system in a first preferred embodiment.

Preferred embodiments according to the present invention provide medical system control devices which can quickly set a medical system to a predetermined use state when a medical system such as an endoscopic system, etc. is erroneously powered off while running, and the medical system is powered on next.

A medical system control device according to a preferred embodiment of the present invention comprises a first control unit (control device) for controlling at least a power supply to a plurality of devices configuring a medical system, a second control unit (centralized control device), the startup process time of which is longer than the first control unit, for controlling the entire medical system, and a storage unit for storing information at the time of an operation termination process for the medical system, which is performed by the second control unit, wherein the first control unit controls a power supply to a predetermined device among the plurality of devices before the startup process of the second control unit is complete according to the information stored in the storage unit in response to the power-on of the medical system.

The devices here are medical devices such as a light source device 12, a video processor 13, an observation monitor 5, an air/water transmission device 14, an electric knife device 21, etc. in the preferred embodiments to be described later. The devices are not limited to these medical devices, and may be constituent elements that can configure a medical system.

With the above described configuration, a power supply is made in a short time to a predetermined device (such as the light source device 12, the video processor 13, and the observation monitor 5, which are essential for an endoscopic examination, in the preferred embodiments to be described later although the predetermined device is not limited to these devices), which is desired to be quickly set to a use state in the medical system by the first control unit, which can perform a startup process in a short time, according to information such as flag information, etc. stored in the storage unit when the medical system is erroneously powered off while running and powered on next.

The above described startup process time is a time until the centralized control device and the control device are enabled to communicate with each other. Further details are provided. The concentrated control device and the control device are connected with a control line. Upon completion of a preparation for a communication, the control device waits until a preparation for a communication on the side of the centralized control device is complete (that is, until a communication permission is given from the centralized control device). When the communication permission is given from the centralized control device, the centralized control device and the control device can communicate with each other.

Preferred embodiments according to the present invention are described hereinafter with reference to the drawings.

First Preferred Embodiment

Conventional examples adopt a configuration where a centralized control, etc. is performed on a general-purpose operational system in normal cases. Therefore, when a user erroneously operates a power switch to power off an endoscopic system while running, it is desired that the system can be quickly set to a minimal use state. However, the conventional examples cannot implement this. That is, the conventional examples have a disadvantage that the system requires a considerable amount of time to be restarted to a use state.

FIG. 1 shows the outside configuration of an endoscopic system in this preferred embodiment. As shown in FIG. 1, a principal portion of the endoscopic system 1 is configured by comprising a system unit 2, a bed 3, an endoscope 4, and an observation monitor 5.

The bed 3 is intended to place a patient not shown. The endoscope 4 is intended to make an endoscopic examination for the patient. The observation monitor 5 is intended to display an endoscopic image.

The system unit 2 comprises an endoscopic system control device 6 (as a medical system control device) (see FIGS. 2 and 3) for performing a centralized operation for the endoscopic system. Additionally, the system unit 2 comprises an operation panel 7, which is connected to the endoscopic system control device 6, for performing a control instruction input operation.

Furthermore, an endoscopic hanger 35 the column of which is attached to the system unit 2 upwardly is formed. Note that the bed 3 is movable in upward and downward directions, and the like.

The endoscope 4 comprises an insertion part 8, an operation part 9, and a universal cable 10. The insertion part 8 is a slim portion to be inserted into a body cavity of a patient, etc. The operation part 9 is a portion provided at the rear end of the insertion part 9. The universal cable 10 is a portion extended from the operation part 9.

In the vicinity of, for example, the rear end of the operation part 9 of the endoscope 4, a scope switch part 11, which can perform an instruction operation such as freeze, etc., is provided. Additionally, a connector at the end of the universal cable 10 of the endoscope 4 is connected to a light source device 12 (see FIGS. 2 and 3) and a video processor 13 (see FIGS. 2 and 3), which are accommodated within the system unit 2.

Figure 2:
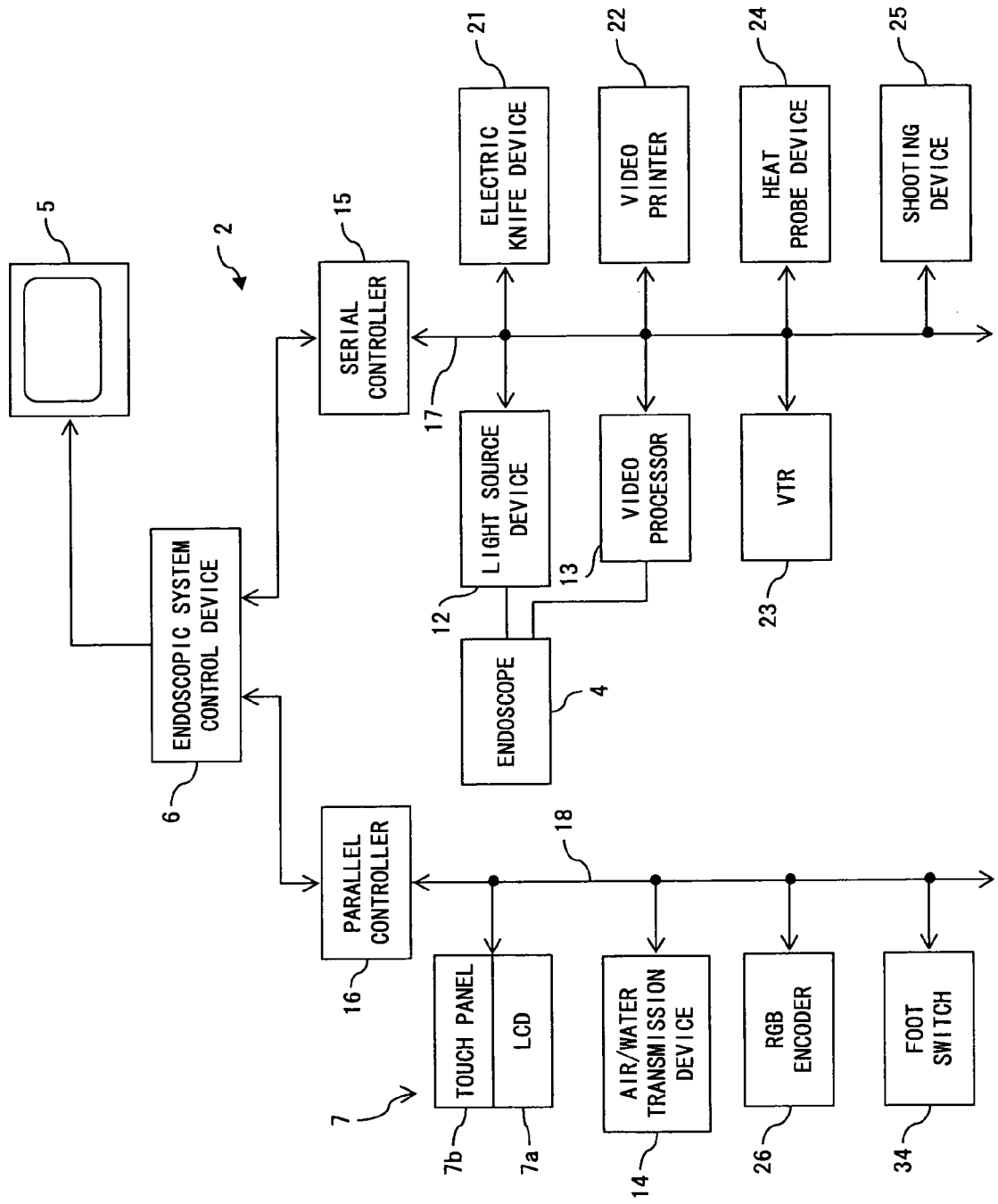
FIG. 2 is a block diagram showing a configuration of a control system of the endoscopic system in the first preferred embodiment.

FIG. 2 is a block diagram showing a configuration of a control system of the endoscopic system in this preferred embodiment. As shown in this figure, the system unit 2 can accommodate the light source device 12, the video processor 13, an air/water transmission device 14, etc.

The light source device 12 supplies illumination light to the endoscope 4. The video processor 13 controls the endoscope 4 or processes an image signal. The air/water transmission device 14 comprises a pump for transmitting air/water via a pipe line of the endoscope 4.

The endoscopic system control device 6, which is one of the constituent elements of the system unit 2, for performing a centralized control for endoscope peripheral devices is configured to perform a centralized control for the endoscope peripheral devices via a serial controller 15 and a parallel controller 16. The serial controller 15 controls a serial interface (abbreviated to a serial I/F). The parallel controller 16 controls a parallel interface (abbreviated to a parallel I/F). Also the observation monitor 5 is connected to the endoscopic system control device 6.

To a serial line 17 via the endoscopic system control device 6 and the serial controller 15, an electric knife device 21, a heat probe (a cauterizing device) 24, a video printer 22, a video tape recorder (abbreviated to VTR) 23, a shooting device 25, etc. can be connected in addition to the above described light source device 12 and video processor 13.

The electric knife device 21 is intended to resect a lesion, etc. The heat probe (cauterizing device) 24 is intended to make a treatment by cauterizing a lesion, etc. The video printer 22 is intended to obtain a hardcopy of a displayed endoscopic image. The VTR 23 is intended to record a video signal. The shooting device 25 is intended to shoot a picture of a displayed endoscopic image.

Additionally, to a parallel line 18 via the endoscopic system control device 6 and the parallel controller 16, an RGB encoder 26 is connected in addition to the above described operation panel 7 and air/water transmission device 14. The RGB encoder 26 is intended to convert a video signal into an RGB video signal.

As shown in FIG. 1, the above described operation panel 7 is provided on the top of the system unit 2. The operation panel 7 is configured by an operation screen display unit and an input detection unit. The operation screen display unit is configured by a display monitor such as a liquid crystal display (abbreviated to LCD) 7a, etc. as shown in FIG. 2. The input detection unit is configured by a transparent touch panel 7b etc. provided in contact with the operation screen display unit.

On the display monitor (LCD 7a), an operation screen on which operation switches for operating the peripheral devices within the system unit 2 are arranged is displayed. With the press (touch) of any of the operation switches on the operation screen, an instruction input operation is detected by the touch panel 7b. Here, the touch panel 7b is configured with switches of many transparent electrodes arranged in the form of a matrix. With this configuration, the touch panel 7b is scanned to detect which switch is pressed and the coordinates of the switch.

FIG. 3 is a block diagram showing a functional configuration when the peripheral devices are controlled with the operation panel in this preferred embodiment. Namely, FIG. 3 shows a functional configuration when the peripheral devices are controlled by user operating the operation panel 7. Operation instruction information is transmitted from the operation panel 7 to the endoscopic system control device 6 (via a user operation). Then, the endoscopic system control device 6 transmits a control signal to a corresponding peripheral device connected to the serial line 17 via the serial controller 15.

To the serial line 17, the light source device 12 is connected via a light source interface (I/F) 27. Additionally, the video processor 13 is connected to the serial line 17 via a video processor interface (I/F) 28. Furthermore, the electric knife device 21 is connected to the serial line 17 via an electric knife device interface (I/F) 29. Still further, the heat probe 24 is connected to the serial line 17 via a heat probe interface (I/F) 30. With this configuration, a centralized control is performed for the peripheral devices according to the control signal transmitted from the endoscopic system control device 6.

The case where the peripheral devices are connected to the serial line 17 is shown in FIG. 3. Also the case where the peripheral devices connected to the parallel line 18 is almost similar.

On the operation panel 7, selection switches are displayed in a screen selection area. Additionally, operation switches, an operation state, a running state, etc. are displayed on the screen of the operation panel 7. Here, any of the selection switches in the screen selection area is selected, whereby an operation screen of a target device desired to be operated is immediately displayed. Additionally, to the endoscopic system control device 6, a set value storage unit 19 for storing set values for each operating user is connected. Therefore, the peripheral devices can be set according to set values suitable for each user.

As described above, the endoscopic system control device 6 inputs/outputs a control signal to/from each of the peripheral devices connected to the endoscopic system control device 6 to control the operations of the peripheral devices. In this case, the operation panel 7 is operated or a switch in the scope switch part 11 provided in the operation part 9 of the endoscope 4 is operated, whereby operation instruction information is transmitted to the endoscopic system control device 6. Then, a control signal is transmitted from the endoscopic system control device 6 to a target peripheral device to control the peripheral device.

When the operation panel 7 is operated, the coordinates of a pressed switch are detected as described above. Then, the endoscopic system control device 6 transmits a control signal of an instruction corresponding to the operation switch displayed on the operation screen to the peripheral device by making a correspondence between the coordinates of the switch and the operation screen. However, a corresponding instruction may be transmitted to the endoscopic system control device 6 as a command based on the coordinates of a pressed switch according to a displayed operation screen on the operation panel 7, and a control signal may be transmitted from the endoscopic system control device 6 to the peripheral device.

As the operation screen displayed on the operation panel 7, a plurality of operation screens, which are divided by functions to control the plurality of peripheral devices of the endoscopic system 1, are prepared. An example of the operation screen for operating the endoscopic system 1 is shown in FIG. 7.

Figure 7:
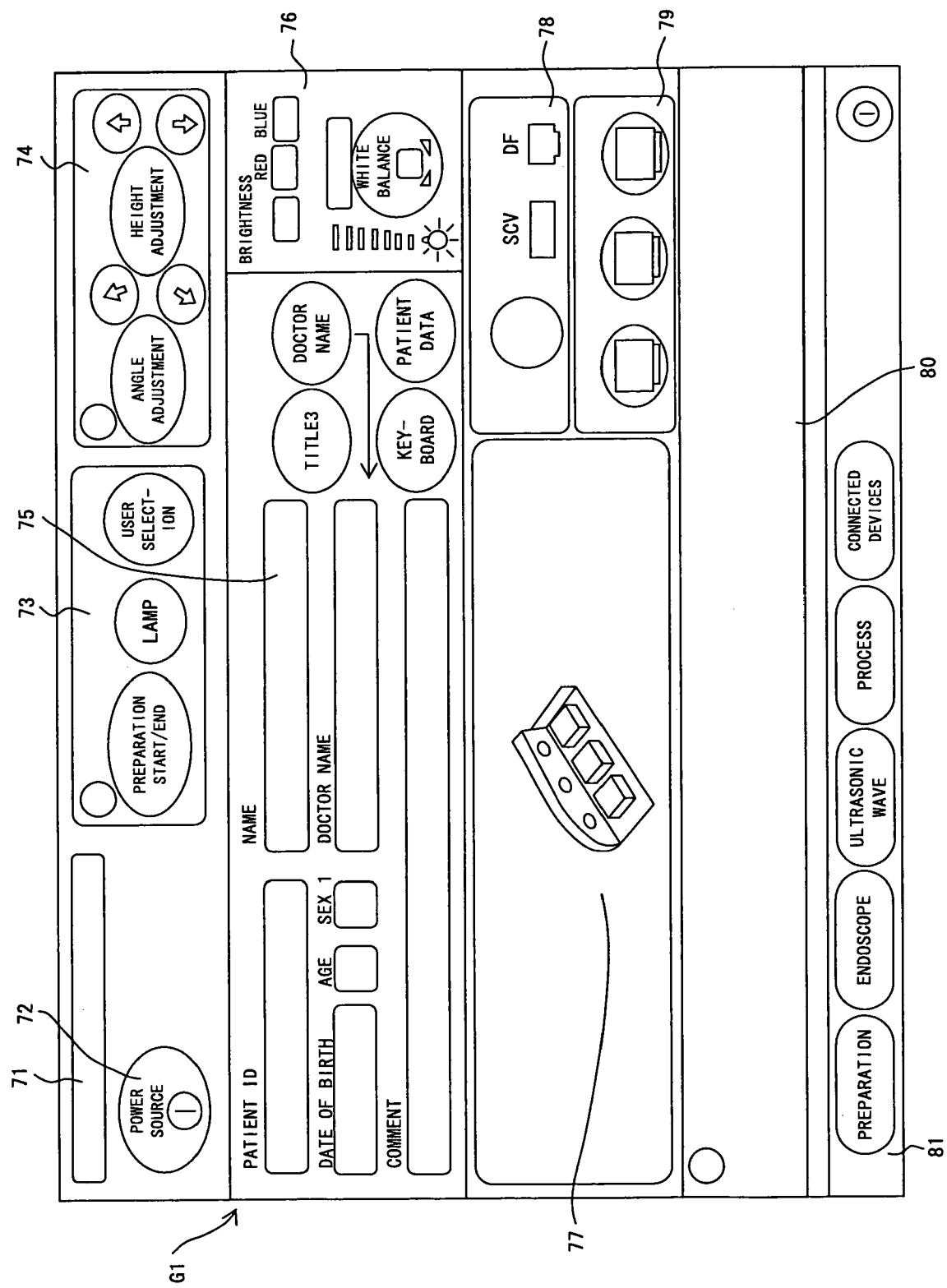
FIG. 7 exemplifies a preparation screen of an operation panel in the first preferred embodiment.

FIG. 7 exemplifies a preparation screen of the operation panel in this preferred embodiment. This preparation screen G1 is displayed, for example, when the endoscopic system 1 is prepared, so that a principal preparation for the endoscopic system 1 can be made.

On this preparation screen G1, a user name display area 71, a connected device power source display area 72, a preparation start/end linkage setting area 73, a bed operation area 74, a patient data display area 75, a video processor basic setting display area 76, a foot switch setting display area 77, a recording destination connection display area 78, a monitor output selection area 79, a user switch display area 80, a screen selection area 81, etc. are displayed.

Additionally, on the operation panel 7, an endoscopic screen, an ultrasonic wave screen, a treatment device screen, and a connected device screen G2 can be displayed. The endoscopic screen is intended to perform various types of settings and operations when the endoscope is used. The ultrasonic wave screen is intended to perform various types of settings and operations when an ultrasonic wave endoscope is used. The treatment device screen is intended to operate a treatment device such as the heat probe 24, the electric knife device 24, etc. The connected device screen G2 is shown in FIG. 8.

Figure 8:
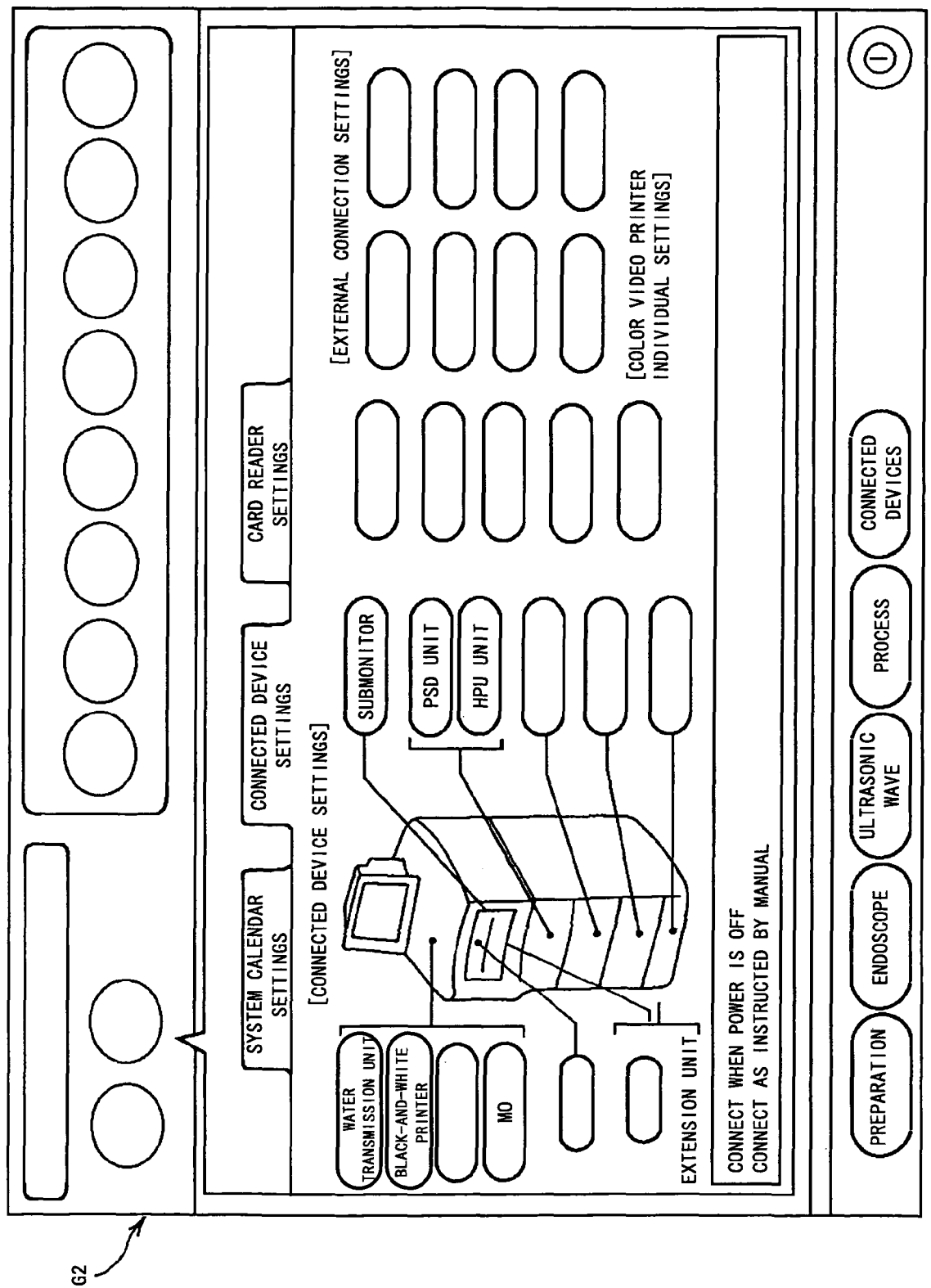
FIG. 8 exemplifies a screen of connected devices on the operation panel in the first preferred embodiment.

FIG. 8 exemplifies the connected device screen on the operation panel in this preferred embodiment. On the connected device screen G2, settings of a connected device can be made.

These operation screens have other operation screens, on which a setting switch of a device or an operation switch the use frequency of which is low is arranged, on demand. These operation screens have a hierarchical structure, and can be operated by being switched. Selection switches displayed in the screen selection area are selected, whereby the endoscopic screen, the ultrasonic wave screen, the treatment device screen, and the connected device screen are displayed, and various types of operations can be performed.

In this preferred embodiment, the endoscopic system control device 6 stores whether the system unit 2 is shut down either normally or abnormally, and a control unit and a control method are configured in the endoscopic system control device 6 to perform a startup operation according to the stored information when the system unit 2 is powered on next.

A configuration of the endoscopic system control device 6 is described below with reference to FIG. 4.

Figure 4:
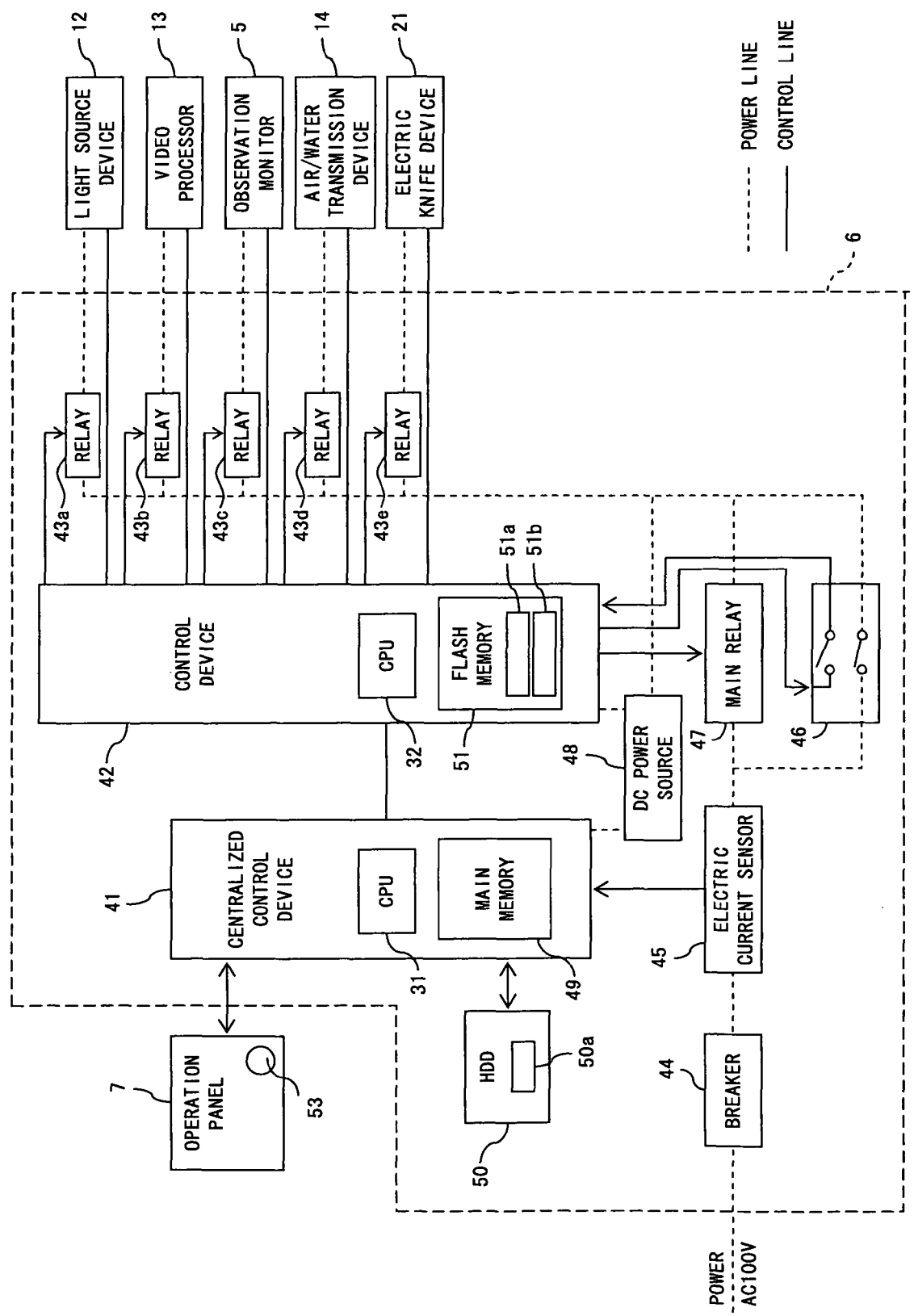
FIG. 4 is a block diagram showing an internal configuration of an endoscopic system control device in the first preferred embodiment.

FIG. 4 is a block diagram showing an internal configuration of the endoscopic system control device in this preferred embodiment. As shown in this figure, the endoscopic system control device 6 according to this preferred embodiment comprises a centralized control device 41 and a control device 42. The centralized control device 41 is configured with a CPU board on which a main CPU 31 is mounted, or the like, and performs a centralized control. The control device 42 is connected to the centralized control device 41 with a control line, and configured with a CPU into which a sub CPU 32 is embedded, or the like. To the control device 42, peripheral medical devices are connected via control lines. Examples of the peripheral medical devices include the light source device 12, the video processor 13, the observation monitor 5, the air/water transmission device 14, and the electric knife device 21.

Additionally, power for operations is supplied to these peripheral devices such as the light source device 12, the video processor 13, . . . , the electric knife device 21, etc. via relays 43a~43e ON/OFF of which are controlled by the control device 42.

Namely, to the peripheral devices such as the light source device 12, the video processor 13, . . . , the electric knife device 21, etc., commercial power is supplied via a breaker 44, an electric current sensor 45, a power switch 46, and the relays 43a~43e within the endoscopic system control device 6.

The power switch 46 is a switch composed of two circuits. A main relay 47 is connected in parallel to the power switch 46. Accordingly, when the power switch 46 is turned on, power is supplied to a DC power source 48. Then, the control device 42 and the centralized control device 41 start up. At the same time, the main relay 47 is kept to be ON as a result of the power supply to the control device 42.

Then, commercial power is supplied to the respective constituent elements via the main relay 47. If the power switch 46 is operated when the main relay 47 is ON, the main relay 47 is turned off via the control device 42. As a result, commercial power is no more supplied to the constituent elements to which commercial power was supplied.

Namely, when the main relay 47 is turned on, commercial power is kept to be supplied to (the input end of) the DC power source 48 via the main relay 47 which is turned on. At the same time, commercial power is also supplied to the peripheral devices such as the light source device 12, the video processor 13, . . . the electric knife device 21, etc. via the relays 43a~43e respectively connected to the main relay 47.

Additionally, to the output ends of the DC power source 48, the centralized control device 41 and the control device 42 are connected, and direct current power required for their operations is respectively supplied.

The electric current sensor 45 detects an electric current supplied from a commercial power source to the endoscopic system control device 6, and transmits this information to the centralized control device 41. Besides, the control device 42 controls ON/OFF of the main relay 47.

Furthermore, a main memory 49 is provided within the centralized control device 41. The main memory 49 is a memory used as a working area where a program is executed, or for holding necessary data. To the centralized control device 41, a hard disk 50 is connected. A program storage area 50a on the hard disk 50 stores at least an operational system program, a shutdown (operation termination) program, and a startup process program. The operational system program is a program as a basic program (basic software). The startup process program is an application program running on the operational system as will be described later. Also the shutdown (operation termination) program is an application program running on the operational system.

When the endoscopic system control device 6 is powered on, the main CPU 31 within the centralized control device 41 reads the startup process program within the hard disk 50 to perform a startup process.

The control device 42 includes a flash memory 51 as a nonvolatile memory that can be electrically erased and reprogrammed. In a storage area 51a of the flash memory 51, a program for the operations of the sub CPU 32 is stored. When the power is turned on, the sub CPU 32 reads the program stored in this storage area 51a, and performs a startup process according to this program.

Additionally, in a storage area 51b of the flash memory 51, a shutdown flag and information about preset values are stored. The shutdown flag is a flag indicating whether the endoscopic system control device 6 of the system unit 2 terminates either normally or abnormally. When (the endoscopic system control device 6 of) the system unit 2 is powered on next, the sub CPU 32 performs a startup process according to the information about the shutdown flag.

Namely, if the shutdown flag indicates the normal termination, the sub CPU 32 performs a process in accordance with a control process of the main CPU 31 after the main CPU 31 of the centralized control device 41 starts up. On the contrary, if the shutdown flag indicates the abnormal termination, the sub CPU 32 on the side of the control device 42 performs a startup process for quickly setting connected devices required for an endoscopic examination to running states according to preset values.

Additionally, in the flash memory 51, information about a consumed current of, for example, each peripheral device in a normal state is stored. The centralized control device 41 receives the information about the consumed current from the control device 42, and stores a first threshold value which is set slightly higher than the maximum current value in the normal state.

Furthermore, in the flash memory 51, the value of a breaker trip current, with which the breaker 44 interrupts an electric current, is stored. The centralized control device 41 stores a second threshold value which is set slightly lower than the value of the breaker trip current.

The centralized control device 41 can also perform a current monitoring operation of whether or not a state of a suitable amount of consumed power is maintained by using the first and the second threshold values.

Additionally, in this preferred embodiment, when an operation screen is displayed, a shutdown button 53 is displayed on the operation panel 7 to ease the shutdown operation.

Utilization of this preferred embodiment adopting such a configuration is described.

Operations performed when the endoscopic system 1 in this preferred embodiment are first described. A user connects the endoscope 4 to the light source device 12, the video processor 13, etc. of the system unit 2. Then, the user turns on the power switch 46, whereby the peripheral devices connected to the system unit 2 are powered on, and an endoscopic examination using the endoscope 4 is ready to be made.

When a therapy or treatment is made, an electric knife, etc. connected to the electric knife device 21 is inserted into a channel of the endoscope 4, and the heat probe 24, etc. is used. As a result, the therapy or treatment can be made. At this time, a centralized control can be performed for the peripheral devices by operating the operation panel 7 provided on the system unit 2.

In this preferred embodiment, when the shutdown process is normally performed and terminated by operating the shutdown button 53, the centralized control device 41 stores the shutdown flag indicating the normal termination in the flash memory 51 as a nonvolatile storage unit.

When the system unit 2 is powered on next, the sub CPU 32 of the control device 42 reads information about the shutdown flag from the flash memory 51. Then, the endoscopic system 1 is started up according to the information about the shutdown flag.

Process procedures at the time of startup in this preferred embodiment are described with reference to FIG. 5.

FIG. 5 is a flowchart showing the startup process performed by the endoscopic system control device. When the power is turned on with the press of the power switch as indicated by step S1, the main relay 47 is turned on as indicated by step S2. In the next step S3, the sub CPU 32 of the control device 42 reads the shutdown flag in the flash memory 51 of the control device 42.

In the next step S4, the sub CPU 32 of the control device 42 determines whether or not the read shutdown flag is a flag indicating the normal termination.

If the sub CPU 32 determines that the shutdown flag is a flag indicating not the last-time normal termination but the last-time abnormal termination, the sub CPU 32 embedded in the control device 42 reads preset values from the flash memory 51 of the control device 42 in step S5.

Then, in the next step S6, the sub CPU 32 of the control device 42 sets a connected device relay for supplying power to set to a running state according to the information about the preset value. Thereafter, the sub CPU 32 sets each device to a running state in the next step S7.

Specifically, the sub CPU 32 controls the light source device 12, the video processor 13, and the relays 43a~43c connected to the observation monitor 5, which are essential for an endoscopic examination, to be turned on. Then, the CPU 32 controls the light source device 12 to light a lamp based on a preset value, so that illumination light is supplied to the side of the endoscope. Additionally, the CPU 32 performs a signal process for an image capturing element of the endoscope 4 based on a preset value to control the video processor 13 so that a video signal is output to the observation monitor 5. Additionally, the CPU 32 controls the observation monitor 5 based on a preset value to display an endoscopic image captured by the image capturing element. As described above, the control device 42 can control the relays and the operations of the connected devices.

Operations of the startup process performed by the sub CPU 32 embedded into the control device 42 are terminated in for example approximately one second, and the endoscopic system control device 6 enters a predetermined running state. Accordingly, the relays 43a~43c are quickly turned on, and the endoscopic system 1 is quickly set to a state where an endoscopic image can be observed.

After approximately for example one minute further elapses, the side of the centralized control device 41 performs a normal startup process to enter a running state. Also the operation panel 7 is displayed at this time.

The main CPU 31 of the centralized control device 41 performs a control process for displaying information about the last-time abnormal termination on the operation panel 7 as indicated by step S8 according to the information about the flag indicating the abnormal termination, and notifies a user that the abnormal termination is made last time. Then, in step S12, the main CPU 31 of the centralized control device 41 clears the shutdown flag indicating the abnormal termination to terminate this startup process.

Or, if the sub CPU 32 determines that the shutdown flag is a flag indicating the last-time normal termination in the determination made in step S4, the sub CPU 32 on the side of the control device 42 waits without performing any operations until the main CPU 31 on the side of the centralized control device 41 starts up. In this case, as indicated by step S9, after the main CPU 31 of the centralized control device 41 reads the startup process program from the hard disk 50 and transfers information about set values, etc. required for the startup process to the main memory 49, it reads the set values from the main memory 49.

Then, in the next step S10, the main CPU 31 of the centralized control device 41 displays the settings of connected devices on the operation panel 7 according to the read information about set values. In this case, the settings of the devices according to the information saving the values set at the time of the last-time termination are normally displayed on the operation panel 7. That is, the state of settings restored from the last-time termination state is normally displayed.

Thereafter, in the next step S11, the main CPU 31 of the centralized control device 41 sets connected device relays. For example, the main CPU 31 of the centralized control device 41 turns off all of the relays at the time of startup. In the next step S12, the main CPU 31 of the centralized control device 41 clears the shutdown flag to terminate this startup process.

If the main CPU 31 of the centralized control device 41 turns off all of the relays in step S11, it may perform a check process for an erroneous connection with a check of a connection state by sequentially turning on the individual connection relays after the startup process in step S12 is terminated. Thereafter, a corresponding relay is turned on for a connected device determined to be normal and power is supplied, whereby an endoscopic examination can be also made.

During the endoscopic examination, the preparation screen G1 shown in FIG. 7 is displayed on the operation panel 7. A principal preparation for the endoscopic system 1 can be made by displaying the preparation screen G1, for example, when the endoscopic system 1 is prepared.

Additionally, on the connected device screen G2 shown in FIG. 8, settings of connected devices can be made. After making these settings, an endoscopic examination can be made.

Figure 9:
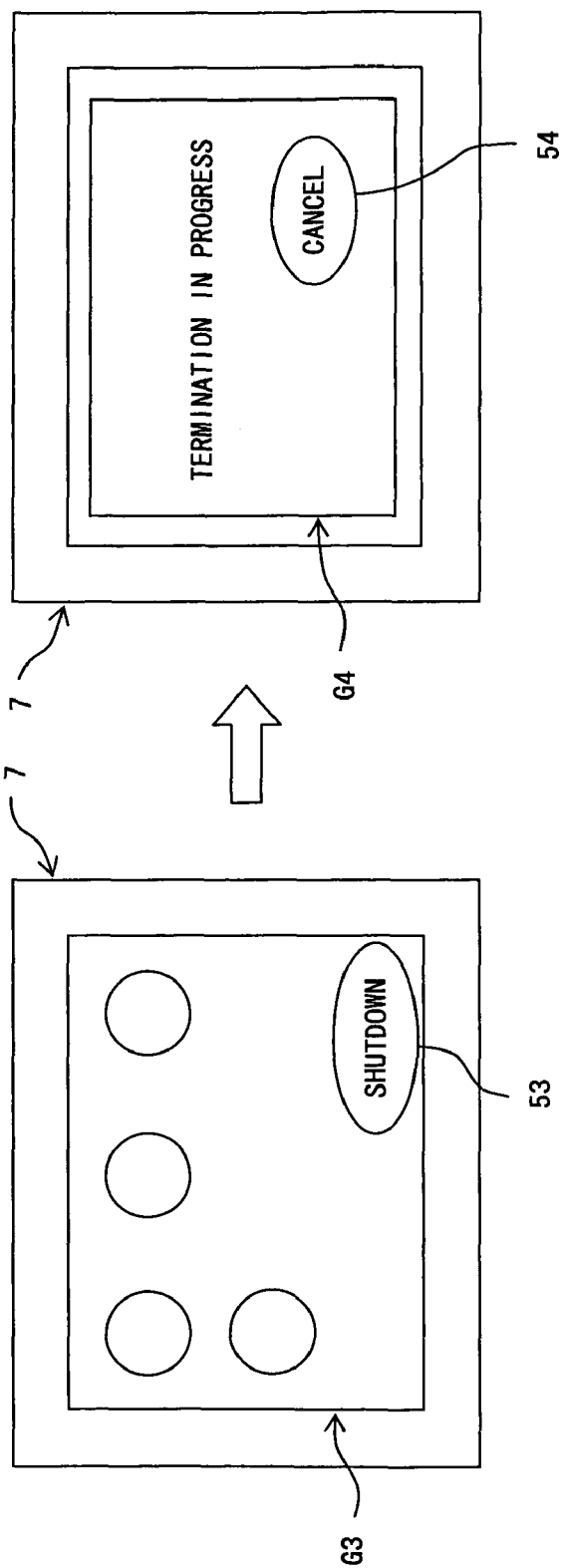
FIG. 9 exemplifies a display when a shutdown button displayed on the operation screen in the first preferred embodiment is operated.

FIG. 9 exemplifies a display when the shutdown button displayed on the operation screen in this preferred embodiment is operated. During an endoscopic examination, the shutdown button 53 is displayed on the operation screen as shown on the left side of FIG. 9. A user such as a surgeon, etc. may touch or press the shutdown button 53 when terminating an endoscopic examination.

In this preferred embodiment, only the case where the shutdown button 53 continues to be pressed, for example, for a few seconds or more is recognized as a shutdown operation by the main CPU 31 in order to reduce erroneous operations of the shutdown button 53.

Operations of the shutdown process by operating the shutdown button 53 are described with reference to FIG. 6.

FIG. 6 is a flowchart showing the shutdown process performed by the endoscopic system control device in this preferred embodiment. As indicated by step S31, a user performs an operation such as continuously touching the shutdown button 53 with a finger, by way of example, for a few seconds or more. Then, the main CPU 31 recognizes this operation as an instruction signal of the shutdown operation.

In the next step S32, the main CPU 31 starts the shutdown process, and notifies the user at this time that the shutdown process is being performed. For example, as indicated by FIG. 9, a message such as "termination in progress", etc. is displayed on the display screen of the operation panel 7 as shown in FIG. 9, whereby the main CPU 32 notifies the user that the shutdown process is being performed.

Additionally, a cancel button 54 is displayed on this display screen. This cancel button 54 is operated, whereby the shutdown process can be also cancelled.

In the next step S33, the main CPU 31 saves information about the set values of respective connected devices in the main memory 49. The information about the set values in the main memory 49 is further saved onto the hard disk 50.

In the next step S34, the main CPU 31 notifies information about the shutdown flag from the centralized control device 41 to the sub CPU 32 of the control device 42. Then, in the next step S35, the sub CPU 32 stores the information about the shutdown flag in the storage area 51b of the flash memory 51.

After storing the information about the shutdown flag in the storage area 51b, the sub CPU 32 turns off the main relay 47 to power off the system unit 2 in the next step S36. In this case, the shutdown flag stored in the storage area 51b of the flash memory 51 is flag information indicating the normal termination.

In this case, the startup process performed when the power is turned on next transfers to step S9 after step S4 of FIG. 5.

In the meantime, if the normal termination with the shutdown button 53 is not made and the power switch 46 is erroneously turned off while the system unit 2 is running, the power is turned off without performing the process shown in FIG. 6. Therefore, the information about the shutdown flag indicating the normal termination is not written to the storage area 51b of the flash memory 51.

In this case, the startup process performed when the power is turned on next transfers to step S5 after step S4 of FIG. 5.

In step S33, the main CPU 31 saves the information about the set values of respective connected devices in the main memory 49. However, this save operation is not limited to this implementation. Namely, the information about the set values of respective connected devices may be saved in the main memory 49, for example, at predetermined time intervals, when the settings of the respective connected devices are changed, when an examination starts or terminates, or when an operation is performed on the operation panel 7.

Such a startup process is performed, whereby a user can obtain the following effects by turning on the power switch 46 when the normal termination process is not performed and the endoscopic system 1 is aborted with an erroneous operation, etc. while running.

Namely, the sub CPU 32 quickly sets connected devices required for an endoscopic examination to running states since the information about the shutdown flag indicating the normal termination is not written. Accordingly, an observation function implemented by the endoscope 4 can be quickly restored.

Second Preferred Embodiment

The second preferred embodiment is described next with reference to FIGS. 10 and 11.

Figure 10:
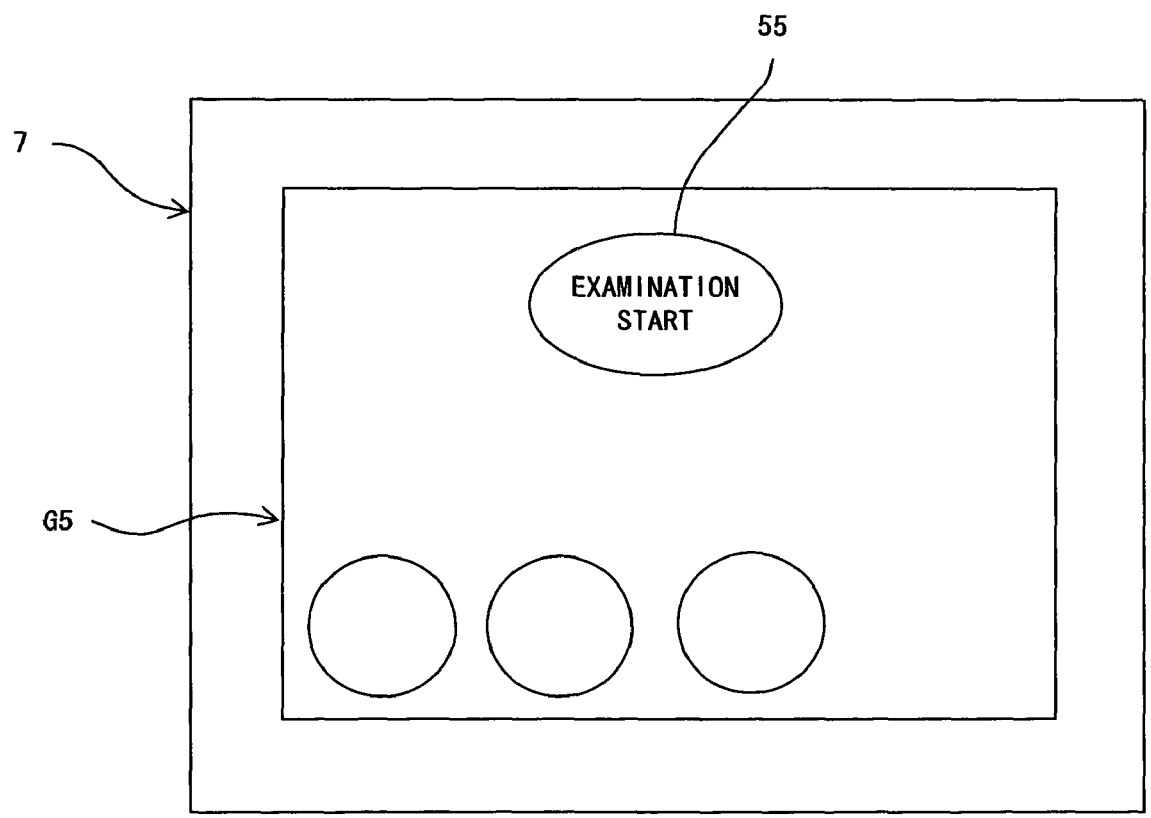
FIG. 10 exemplifies a screen of an examination start in a second preferred embodiment.

FIG. 10 exemplifies a screen of an examination start in this preferred embodiment. In this preferred embodiment, on an operation screen of an operation panel 7, an examination start button 55 is displayed as shown in FIG. 10. A user such as a surgeon, etc. operates the examination start button 55 to start an endoscopic examination.

In this preferred embodiment, a startup process is performed by further using information about an in-progress-examination flag, which indicates that an (endoscopic) examination is being made, with the operation of the examination start button 55. That is, when the examination start button 55 is operated, information about the in-progress-examination flag is written, for example, to a storage area 51b of a flash memory 51 of a control device 42. Namely, information about a shutdown/in-progress-examination flag is written to the storage area 51b.

The information about the in-progress-examination flag is naturally cleared (to terminate an endoscopic examination) when the normal termination is made with a shutdown button 53. Therefore, if abnormal termination such as an erroneous operation of a power switch 46 during an endoscopic examination, etc. is made, the in-progress-examination flag is written to the storage area 51b of the flash memory 51. Therefore, the abnormal termination is proved to be made during the examination.

Even if the abnormal termination such as an erroneous operation of the power switch 46 prior to an examination start is made when the system unit 2 is set to a running state, the necessity to quickly set to an in-progress-examination state is small. Therefore, a startup process almost similar to the normal termination is performed in this preferred embodiment. The startup process in this case is shown in FIG. 11.

Figure 11:
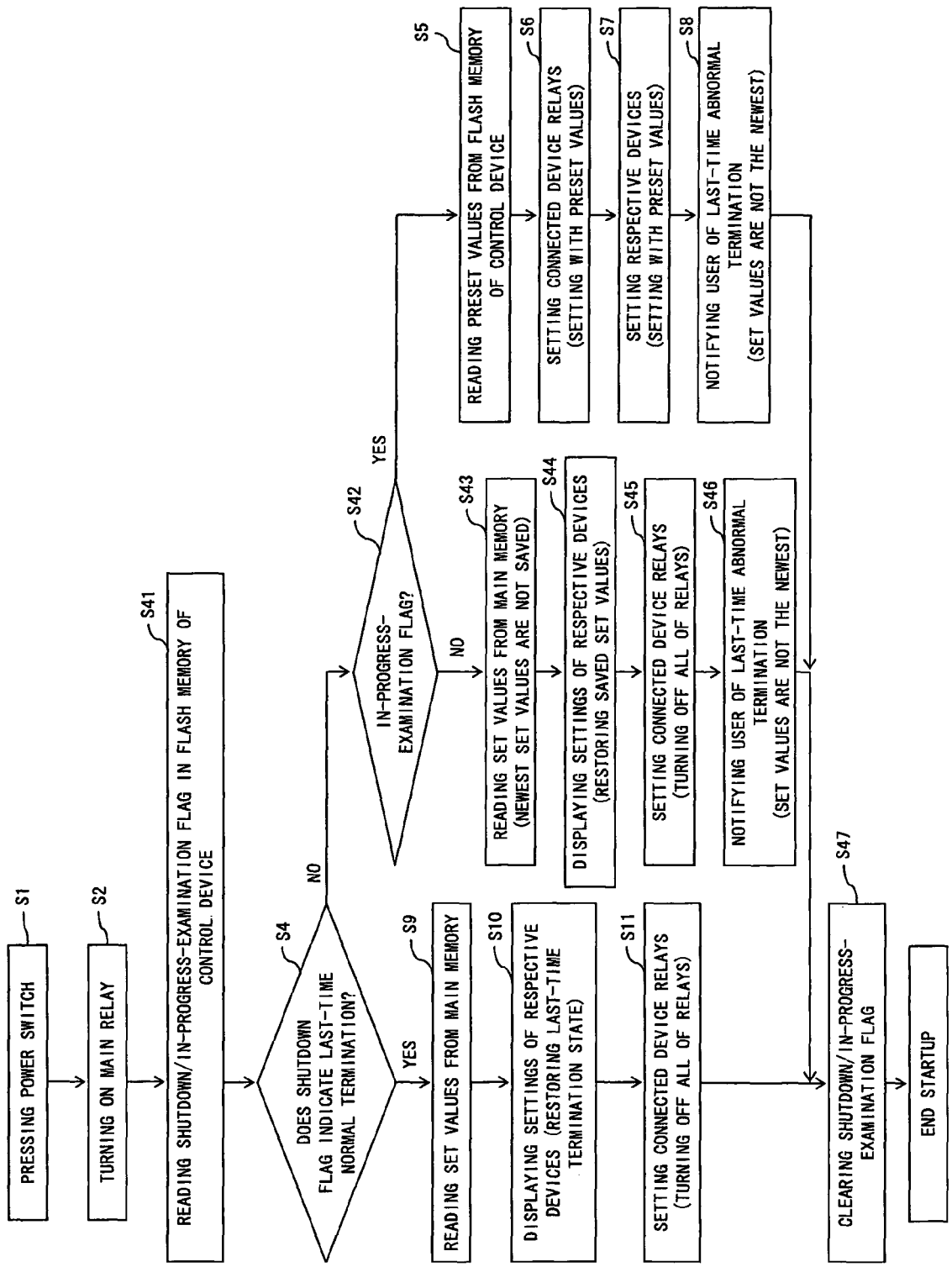
FIG. 11 is a flowchart showing a startup process in the second preferred embodiment.

FIG. 11 is a flowchart showing the startup process performed in this preferred embodiment. In this startup process, step S41 is performed instead of the process in step S3 of the startup process shown in FIG. 5. If a result of the determination made in step S4 is "NO" in the startup process shown in FIG. 5, a determination process in step S42 is performed before the flow transfers to the process of step S5.

If a result of the process for determining whether or not the flag is an in-progress-examination flag in step S42 is "YES", the flow transfers to step S5. Or, if the result of the determination process is "NO", the flow transfers to steps S43~S46. Additionally, step S47 is performed instead of step S12.

Further details are provided below.

When the power is turned on with the press of the power switch as indicated by step S1, a main relay 47 is turned on as indicated by step S2. In the next step S41, the sub CPU 32 of the control device 42 reads the shutdown/in-progress-examination flag in the flash memory 51 of the control device 42.

In the next step S4, the sub CPU 32 of the control device 42 determines whether or not the shutdown flag indicates the last-time normal termination in the read shutdown/in-progress-examination flag.

If the sub CPU 32 determines that the shutdown flag indicates not the last-time normal termination but abnormal termination, the sub CPU 32 of the control device 42 determines in step S42 whether or not the in-progress-examination flag exists. If the in-progress-examination flag exists, the flow transfers to step S5. Processes in steps S5~S8 are similar to those in the first preferred embodiment.

After step S8, the main CPU 31 of the centralized control device 41 clears the shutdown/in-progress-examination flag as indicated by step S47 to terminate this startup process.

Or, if the in-progress-examination flag does not exist in the determination made in step S42, this indicates that the abnormal termination is made while an examination is not being made. Therefore, the startup process similar to that of the normal termination is basically performed (although the abnormal termination is notified).

Namely, as indicated by step S43, after the main CPU 31 of the centralized control device 41 reads a startup process program from the hard disk 50 and transfers information about set values, etc. required for a control operation to the main memory 49, the main CPU 31 reads the set values from the main memory 49. Note that, however, the newest set values are not saved.

Then, in the next step S44, the main CPU 31 of the centralized control device 41 displays the settings of respective connected devices on the operation panel 7 according to the read information about the set values. Namely, the saved set values are restored and displayed (although they are not the newest).

In the next step S45, the main CPU 31 of the centralized control device 41 sets connected devices relays. In this case, all of the relays are turned off. In the next step S46, the main CPU 31 of the centralized control device 41 notifies a user of the last-time abnormal termination. In this case, it may be notified that the set values are not the newest. Then, the flow proceeds to step S47.

If the shutdown flag indicates the last-time normal termination in the determination made in step S4, the flow proceeds to step S9 in a similar manner as in the first preferred embodiment. After steps S9~S11 are performed, the flow transfers to step S47.

According to this preferred embodiment where such a startup process is performed, when the endoscopic system 1 is powered on next while the endoscopic system 1 is running, information about whether or not an examination is actually being made is used, whereby the endoscopic system 1 can be set to a running state more suitably. Other effects produced by this preferred embodiment are similar to those in the fist preferred embodiment.

Third Preferred Embodiment

The third preferred embodiment is described next with reference to FIGS. 12 and 14.

Figure 12:
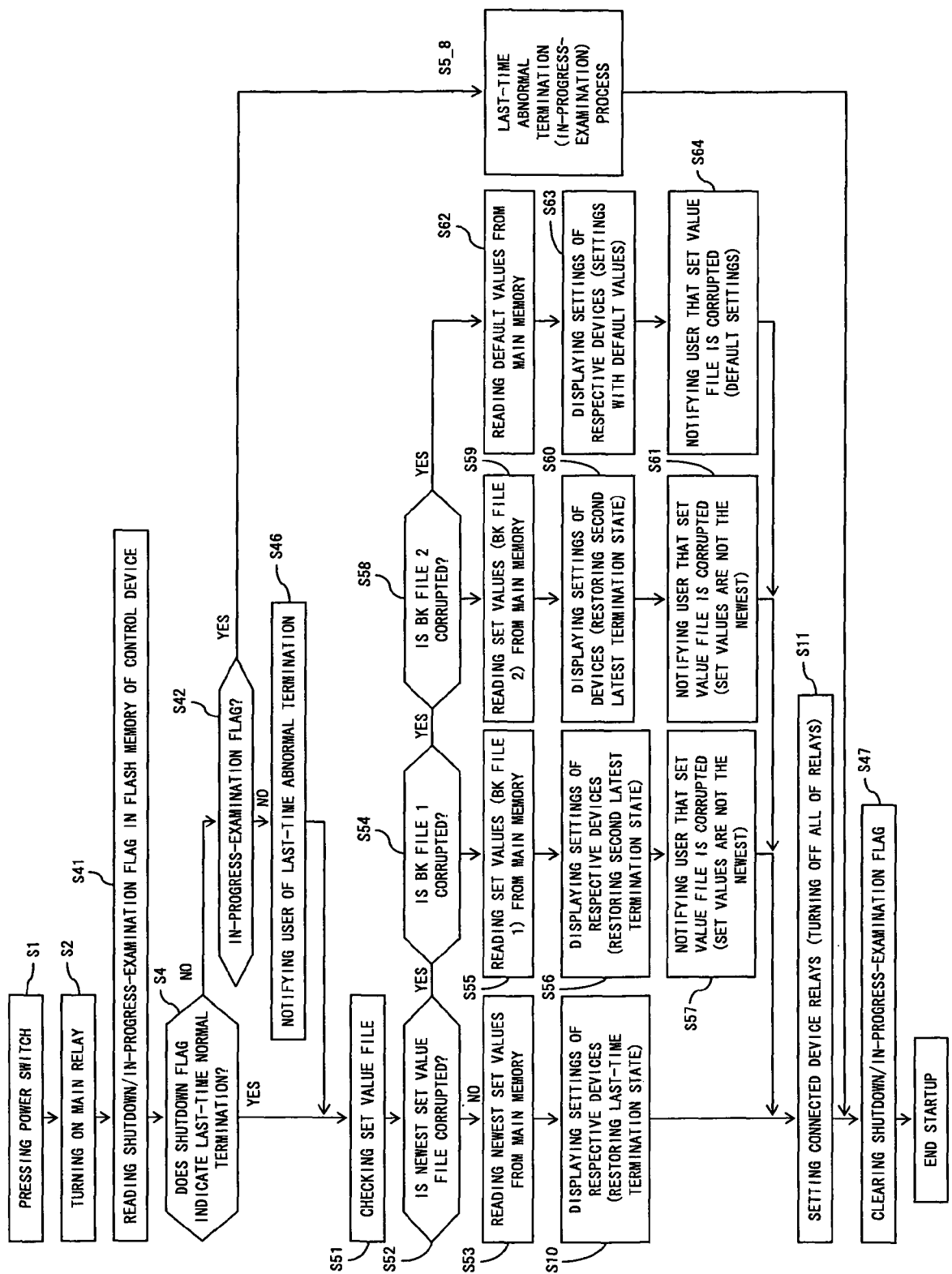
FIG. 12 is a flowchart showing a startup process in a third preferred embodiment.

FIG. 12 is a flowchart showing a startup process performed in this preferred embodiment. In this preferred embodiment, a check process for a set value file is further performed when the startup process is performed in the configuration of the second preferred embodiment. If the newest set value file is corrupted in the check process, more suitable values are set, for example, by checking whether or not a backup file 1 set and saved preceding the newest file is corrupted. Accordingly, the same processes as those in the second preferred embodiment are denoted with the same reference numerals.

After the power is turned on with the press of a power switch as indicated by step S1 of FIG. 12, processes in steps S2, S41, S4, and S42 are performed in a similar manner as in the second preferred embodiment.

If an in-progress-examination flag exists in a determination made in step S42, processes in steps S5~S8 (abbreviated to S5_8 in FIG. 12) for the last-time abnormal termination (while an examination is being made) are performed in a similar manner as in the second preferred embodiment.

Or, if the in-progress-examination flag does not exist in the determination made in step S42, the main CPU 31 of the centralized control device 41 notifies a user of the last-time abnormal termination (while an examination is not being made) as indicated by step S46. Then, the flow proceeds to step S51. Also if a shutdown flag indicates the last-time normal termination in the determination made in step S4, the flow proceeds to step S51.

In step S51, the main CPU 31 of the centralized control device 41 starts a check process for a set value file.

Then, in step S52, the main CPU 31 of the centralized control device 41 determines whether or not the newest set value file is corrupted. If the newest set value file is not corrupted, the main CPU 31 of the centralized control device 41 reads the newest set values from the main memory 49 in step S53. Thereafter, processes in steps S10, S11, and S47 are performed in a similar manner as in the second preferred embodiment.

Or, if the newest set value file is corrupted in step S52, the main CPU 31 of the centralized control device 41 determines in step S54 whether or not a backup file 1 (abbreviated to BK file 1 in FIG. 12) saving the second newest set values is corrupted. If the backup file 1 is not corrupted, the main CPU 31 of the centralized control device 41 reads the set values of the backup file 1 from the main memory 49 in step S55.

In the next step S56, the main CPU 31 of the centralized control device 41 displays the settings of respective devices on the operation panel 7. In this case, the second latest termination state is restored. In the next step S57, the main CPU 31 of the centralized control device 41 notifies the user that the set value file is corrupted. For example, it is notified that the set values are not the newest. Then, the flow transfers to step S11.

Or, if the backup file 1 is corrupted in the determination made in step S54, the flow transfers to step S58, in which the main CPU 31 of the centralized control device 41 determines whether or not a backup file 2 (abbreviated to BK file 2 in FIG. 12) saving the set values newest second to the backup file 1 is corrupted. If the backup file 2 is not corrupted, the main CPU 31 of the centralized control device 41 reads the set values of the backup file 2 from the main memory 49.

In the next step S60, the main CPU 31 of the centralized control device 41 displays the settings of the respective devices on the operation panel 7. In this case, the third latest termination state is restored. In the next step S61, the main CPU 31 of the centralized control device 41 notifies the user that the set value file is corrupted. For example, it is notified that the set values are not the newest. Then, the flow transfers to step S11.

Or, if the backup file 2 is corrupted in the determination made in step S58, the main CPU 31 of the centralized control device 41 reads default values from the main memory 49 in step S62.

In the next step S63, the main CPU 31 of the centralized control device 41 displays the settings of respective devices on the operation panel 7. In the next step S64, the main CPU 31 of the centralized control device 41 notifies the user that the set value file is corrupted. For example, it is notified that the set values are default values. Then, the flow proceeds to step S11.

In this way, the system unit 2 is started up. Then, an endoscopic examination can be made.

In the meantime, when an endoscopic examination is made and the shutdown button 53 is pressed, the main CPU 31 of the centralized control device 41 saves information about set values in the main memory 49. A save process for the set values in this case is described with reference to FIGS. 13 and 14.

FIG. 13 is a flowchart showing the save process for a set value file in this preferred embodiment. FIG. 14 explains the operations performed in FIG. 13. Once the save process for set values is started as shown in FIG. 13, the main CPU 31 of the centralized control device 41 first creates a new file in the main memory 49 to save the currently newest set values as indicated by step S71.

Figure 14:
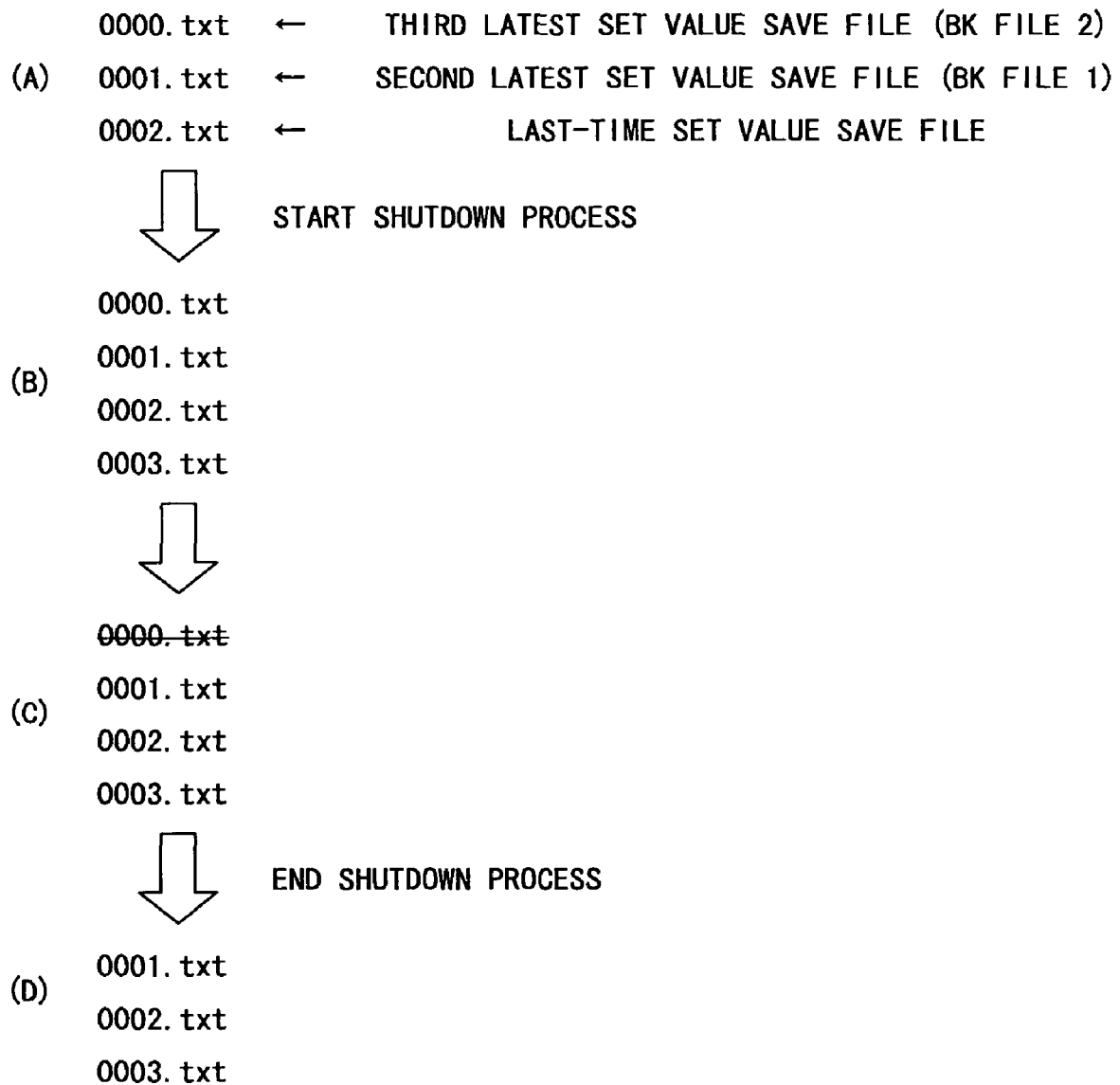
FIG. 14 explains the operations performed in FIG. 13.

In this case, the set value files saved in the main memory 49 before the shutdown process is started are assumed to be those shown in (A) of FIG. 14. Description is provided by assuming that the set value files are respectively 0002.txt as the last-time set value save file, 0001.txt as the second latest set value save file, and 0000.txt as the third latest set value save file in this case.

The new file is created as described above, whereby 0003.txt as the newest set value save file is created as shown in (B) of FIG. 14.

In the next step S72, the main CPU 31 of the centralized control device 41 deletes 0000.txt as the third latest set value save file, which is the oldest set value save file. Namely, 0000.txt as the third latest set value save file is deleted as shown in (C) of FIG. 14.

Accordingly, the three save files are left in the main memory 49 as shown in (D) of FIG. 14. The save process for set values is performed in this way, thereby eliminating the need to access 0001.txt and 0002.txt as the set value save files. As a result, the files can be prevented from being corrupted at the time of an access, etc., and their reliability can be improved.

In the above provided description, the save process for a set value save file is described in the case where the main memory 49 is used. However, it is evident that a save process for a set value save file on the hard disk 50 is also applicable. Additionally, the three save files are left in this preferred embodiment. However, the number of files to be left is not limited to 3. Two or four files or more may be left depending on a use purpose.

The above preferred embodiments are described by assuming the case of the endoscopic system 1 using the endoscope 4. However, the present invention is applicable to other medical systems such as an ultrasonic wave diagnostic system, a medical microscopic system, etc. in a similar manner.

According to the present invention, a power supply can be made to a predetermined medical device in a short time when a medical system is erroneously powered off while running and powered on next.

As described above, according to the present invention, a power supply is made to a medical device desired to be quickly set to a running state before a main control device completes a startup process, which requires a considerable amount of time until startup when power is again turned on in a case where a power switch is erroneously turned off while an endoscope, etc. is running in a medical system. As a result, a predetermined function such as observation of an endoscopic image, etc. is quickly implemented.

What is claimed is:

1. A medical system control device, comprising:
   a first control unit for controlling at least a power supply to a plurality of devices configuring a medical system;
   a second control unit, a startup process time of which is longer than said first control unit, for controlling the entire medical system; and
   a storage unit for storing information at the time of an operation termination process for the medical system, which is performed by said second control unit, wherein
   said first control unit controls a power supply to a predetermined device among the plurality of devices before the startup process of said second control unit is complete, according to the information stored in said storage unit in response to power-on of the medical system.

2. The medical system control device according to claim 1, wherein
   said first control unit controls operations of the predetermined device among the plurality of devices before the startup process of said second control unit is complete, according to the information stored in said storage unit in response to the power-on of the medical system.

3. The medical system control device according to claim 1 or 2, the medical system being an endoscopic system using an endoscope.

4. The medical system control device according to claim 3, wherein
   said storage unit stores information about an examination start operation using the endoscope.

5. The medical system control device according to claim 1, wherein
   the information at the time of the operation termination process is flag information indicating whether or not the operation termination process is normally performed by said second control unit.

6. The medical system control device according to claim 1, wherein
   said storage unit prestores information about the predetermined device when the power supply is controlled.

7. The medical system control device according to claim 1, wherein
   said first control unit performs a startup process for a power supply for the predetermined device after the startup process is performed by said second control unit, if the information at the time of the operation termination process is flag information indicating that the operation termination process is normally performed.

8. A medical system startup control method used when a medical system is powered on, comprising:
   a storing step of storing information about whether or not an operation termination process in the medical system is normally performed;
   a determining step of determining whether or not the operation termination process is normally performed by reading the information when the medical system is powered on;
   a first startup process step of controlling a power supply to a predetermined device if the operation termination process is determined not to be normally performed in said determining step; and
   a second startup process step of performing a startup process which takes longer time than said first startup process step in accordance with a case of a normal termination if the operation termination process is determined to be normally performed in said determining step.

9. The medical system startup control method according to claim 8, wherein
   in said first startup process step, operations of the predetermined device are controlled if the operation termination process is determined not to be normally performed in said determining step.

10. The medical system startup control method according to claim 8, wherein in said storing step, information about the predetermined device is stored in addition to the information about whether or not the operation termination process is normally performed.

11. The medical system startup control method according to claim 8, wherein in said storing step, information about whether or not the medical system is practically set to a running state is stored.

\* \* \* \* \*